United States Patent [19]

Ron et al.

[11] Patent Number: 5,171,579
[45] Date of Patent: Dec. 15, 1992

[54] FORMULATIONS OF BLOOD CLOT-POLYMER MATRIX FOR DELIVERY OF OSTEOGENIC PROTEINS

[75] Inventors: Eyal Ron, Lexington, Mass.; Robert G. Schaub, Pelham, N.H.; Thomas J. Turek, Boston, Mass.

[73] Assignee: Genetics Institute, Inc., Cambridge, Mass.

[21] Appl. No.: 776,514

[22] Filed: Oct. 11, 1991

[51] Int. Cl.$^5$ ............................................. A61K 31/765
[52] U.S. Cl. ...................................... 424/486; 424/484
[58] Field of Search .................. 424/484, 486; 524/17; 530/350

[56] References Cited

U.S. PATENT DOCUMENTS

| | | | |
|---|---|---|---|
| 4,186,448 | 2/1980 | Brekke | 623/16 |
| 4,563,489 | 1/1986 | Urist | 524/17 |
| 4,639,366 | 1/1987 | Heller | 424/484 |
| 4,902,296 | 2/1990 | Bolander et al. | 623/16 |
| 4,975,526 | 12/1990 | Kuberasampath et al. | 530/350 |
| 5,013,649 | 5/1991 | Wang | 530/350 |
| 5,024,841 | 6/1991 | Chu | 424/484 |

FOREIGN PATENT DOCUMENTS 8904646  6/1989  World Int. Prop. O. .
9118558 12/1991  World Int. Prop. O. .

OTHER PUBLICATIONS

Hollinger, J., J. of Biomed. Mat. Res. 17:71–82 (1983).
Wood, D., Int. J. of Pharm. 7:1–18 (1980).
Kitchell, J. et al., Methods in Enzymology 112:436–448 (1985).
Johnson, E. et al., J. Jpn. Orthop. Assoc. 63:613–620 (1989).
Ferguson, D. et al., Clin. Ortho. and Related Res. 219:251–258 (1987).

Primary Examiner—Thurman K. Page
Assistant Examiner—William E. Benston, Jr.
Attorney, Agent, or Firm—Thomas J. DesRosier; Patricia A. McDaniels

[57] ABSTRACT

A composition comprising a pharmaceutically acceptable admixture of an osteogenic protein; a porous particulate polymer matrix; and an osteogenic protein-sequestering amount of blood clot.

20 Claims, No Drawings

FORMULATIONS OF BLOOD CLOT-POLYMER MATRIX FOR DELIVERY OF OSTEOGENIC PROTEINS

BACKGROUND OF THE INVENTION

The subject invention relates to the field of osteogenic proteins and pharmaceutical formulations thereof. More particularly, the subject invention involves pharmaceutical formulations designed to sequester osteogenic protein in-situ for a time sufficient to allow the protein to induce cartilage and/or bone formation.

Osteogenic proteins are those proteins capable of inducing, or assisting in the induction of, cartilage and/or bone formation. Many such osteogenic proteins have in recent years been isolated and characterized, and some have been produced by recombinant methods. For example, so-called bone morphogenic proteins (BMP) have been isolated from demineralized bone tissue (see e.g. Urist U.S. Pat. No. 4,455,256); a number of such BMP proteins have been produced by recombinant techniques (see e.g. Wang et al. U.S. Pat. No. 4,877,864 and Wang et al. U.S. Pat. No. 5,013,549); a family of transforming growth factors (TGF-$\alpha$ and TGF-$\beta$) has been identified as potentially useful in the treatment of bone disease (see e.g. Derynck et al., U.S. Ser. No. 695,494 U.S. Pat. No. 5,125,978 which corresponds to EP 154,434); a protein designated Vgr-1 has been found to be expressed at high levels in osteogenic cells (see Lyons et al. (1989) Proc. Nat'l. Acad. Sci. USA 86, 4554-4558); and proteins designated OP-1, COP-5 and COP-7 have purportedly shown bone inductive activity (see Oppermann, et al. U.S. Pat. No. 5,001.691).

Various attempts have been made at developing formulations designed to deliver osteogenic proteins to a site where induction of bone formation is desired For example, certain polymeric matrices such as acrylic ester polymer (Urist, U.S. Pat. No. 4,526,909) and lactic acid polymer (Urist, U.S. Pat. No. 4,563,489) have been utilized, but these formulations do not sequester the osteogenic protein for a time sufficient to optimally induce bone formation. Collagen matrices have also been used as delivery vehicles for osteogenic proteins (see e.g. Jeffries, U.S. Pat. No. 4,394,370), but collagen frequently causes undesirable antigenic reactions in patients.

SUMMARY OF THE INVENTION

Applicants have surprisingly discovered that osteogenic proteins can be sequestered at a site where bone inducing activity is desired using blood clot in the absence of an antifibrinolytic agent, provided that a porous particulate polymer matrix is incorporated into the formulation. Therefore, more particularly, the subject invention provides a composition comprising a pharmaceutically acceptable admixture of an osteogenic protein; a porous particulate polymer matrix and an osteogenic proteinsequestering amount of blood clot.

DETAILED DESCRIPTION OF THE INVENTION

The osteogenic proteins useful in the practice of the subject invention are well known to those skilled in the art and include those discussed above. The preferred osteogenic proteins for use herein are those of the BMP class identified as BMP-1 through BMP-8 in U.S. Pat. No. 4,877,864; U.S. Pat. No. 5,013,649; copending U.S. patent applications Ser. No. 437,409, aband. Ser. No. 490,033, and Ser. No. 438,919 (all three WO 90/11366 published Oct. 4, 1990); and Ser. No. 525,357. All references cited herein are hereby incorporated by reference. The most preferred is BMP-2, the full length cDNA sequence and the ultimate mature protein sequence described in detail in the '649 patent. Of course, combinations of two or more of such osteogenic proteins may be used, as may fragments of such proteins that also exhibit osteogenic activity. Such osteogenic proteins are known to be homodimeric species, but also exhibit activity as mixed heterodimers. Recombinant proteins are preferred over naturally occurring isolated proteins. The amount of osteogenic protein useful herein is that amount effective to stimulate increased osteogenic activity of infiltrating progenitor cells, and will depend upon the size and nature of defect being treated as discussed in more detail below, such amounts being orders of magnitude less than the amount of polymer matrix employed, generally in the range of 1-30 $\mu$g of protein for each 10 mg of polymer matrix employed.

The osteogenic proteins can be utilized in the form of a pharmaceutically acceptable solution (including reconstitution from a lyophilized form). It is optimal to solubilize the osteogenic protein at concentrations of at least about 2 mg/ml, preferably about 4 mg/ml, so that a pharmaceutically effective amount of protein can be delivered without undue volumes of carrier being necessary. Amino acids having a net positive charge (e.g. net 1+ species such as arginine, lysine and the ethyl esters of glycine and beta-alanine), preferably a net 2+ charge (e.g. the ethyl ester of histidine, the methyl esters of lysine and arginine, and agmatine), are useful in this regard. Amino acids having a net zero charge are useful in this regard provided that the positive charge of the compound is sufficiently distant (at least 2-3 $CH_2$ units away) from the neutralizing negative charge (e.g. net neutral species such as gamma-amino butyric acid, beta-amino propionic acid, glycine and glycine-glycine dipeptide). Other solubilizing agents useful herein include dextran sulfate, guanidine, heparin and sodium chloride. For use in solubilizing BMP-2, the preferred solubilizing agents are arginine and histidine (including esters thereof). The solubilizing agents are used in concentrations of 50-600 mM, preferably 300-500mM. Various well known methods may be used to compound the osteogenic protein and solubilizing agents for use herein, including but not limited to dialysis, gel filtration, and hydrophobic interaction chromatography.

The polymer matrix component useful in the practice of the subject invention is a polymeric material that can be formed into porous particles as described below thereby providing in-situ scaffolding for the osteogenic protein, while having biodegradable properties allowing for replacement by new bone growth. Examples are polymers of orthoesters, anhydrides, propylene-cofumarates, or a polymer of one or more $\alpha$-hydroxy carboxylic acid monomers, (e.g. $\alpha$-hydroxy acetic acid (glycolic acid) and/or $\alpha$-hydroxy propionic acid (lactic acid)). The latter can be employed in its d- or l-form, or as a racemic mixture, the racemic mixture being preferred. When a copolymer of lactic acid and glycolic acid is employed (PLGA), the molar ratio of monomers can range from 1:99 to 99:1 depending upon the desired bio-life which in turn depends upon the clinical indication being addressed, as more than 50% of either monomer gives longer bio-life (slower biodegradation). The molecular weight of the polymer can range from about 1,000 to 100,000 (relative to polystyrene in CHCl$_3$) with 30-50K being preferred when a 50:50 copolymer is employed. The higher the MW the slower the biodegradation.

The polymeric matrix component of the subject invention is used in the form of highly porous to hollow (with surface porosity) particles, hereinafter collectively referred to as "porous particles." These porous particles are generally spherical having diameters of 150 to 850 microns, preferably 150-500 microns, most preferably 150-300 microns. This particle size creates sufficient spacing between particles to allow mammalian osteoprogenitor cells to infiltrate and be positively influenced by (evidenced by an increase in osteogenic activity/bone growth rate) the osteogenic protein. Particles useful herewith have a porosity such that the surface area of the particles is between about 0.01 m$^2$/g to about 4.0 m$^2$/g which represents an increase of about 2-100 fold over the surface area of non-porous particles of comparable size. The preferred method of production is, generally speaking, a solvent evaporation or solvent exchange process comprising dissolving the polymer (in e.g. CH$_2$Cl$_2$), and adding a porosigen (composition capable of imparting porosity) such as NaCl, mannitol or sucrose. This solution is added to an excess aqueous solution containing surfactant such as poly(vinyl alcohol) with controlled stirring. The resultant porous particles are hardened by extracting residual solvent, and dried. The porous nature of the particles creates sufficient surface area for protein adsorption and increases biodegradation, the desirable extent of both being dependent upon the clinical indication being addressed. For example, PLGA particles useful in the subject invention made utilizing 50% NaCl as a porosigen have a surface area of between about 0.2 and 1.0 m$^2$/g; and particles made using sucrose as a porosigen have a surface area of between about 0.04 and 0.09 m$^2$/g. Surface area can be measured by any conventional technique. For example, BET surface area analysis can be employed using a Micrometrics ASAP 2000 system that measures surface area based upon adsorption and desorption of Krypton gas at the surface and within the pores of the solid sample. The unit calculates and prints out the surface area:

$$\frac{1}{VA[(P_0/P) - 1]} = \frac{C - 1}{V_m C} (P/P_0) + \frac{1}{V_m C}$$

$V$ = volume absorb at pressure $P$  
$P_0$ = saturation pressure  
$P/P_0$ = relative pressure  
$P$ = pressure  
$C$ = constant  
$A$ = gas cross sectional area  
$V_m$ = Monolayer Capacity By plotting $$\frac{1}{VA((P_0/P) - 1)} \text{ vs } P/P_0,$$

the slope being $$\frac{C - 1}{V_m C}$$

and the intercept being $$\frac{1}{V_m C},$$

the surface area $$S_t = \frac{V_m N A}{V}$$

where N = Avogadrio's number and V = molar volume. The amount of porous particles will, of course, depend upon the size of the defect being treated, and on the effective amount required to adsorb the osteogenic protein, that amount generally being about 250 mg of porous particles (assuming 0.25g/cc density) for each 1 ml of defect.

The protein-sequestering material useful in the practice of the subject invention is pharmaceutically acceptable human blood, preferably autologous blood. When added to an osteogenic protein/porous particle mixture, the blood clots to form a malleable composite wherein the adsorbed protein is sequestered within the matrix for a time sufficient to allow the protein to increase the otherwise natural rate of osteogenic activity of the infiltrating mammalian progenitor cells. In the absence of such blood clot, osteogenic protein desorbs from the PLGA particles in-situ at a rate such that the osteoinducing effect of the protein is not clinically significant. The ratio of blood to porous particles useful herein is 1:1 to 1:2 (V:V), preferably 1:1.5 (v:v), which represents the amount necessary to prevent desorbtion from the polymer matrix, yet not so much that the progenitor cells are prevented from infiltrating the matrix, thereby providing the protein the opportunity to assist the osteogenic activity of the progenitor cells. For each ml defect, the amount of blood required will therefore generally be about 0.5-1.0 ml. In cases where large doses of osteogenic protein are employed, clot facilitating agents such as thrombin may be employed to offset the dilution effect of the osteogenic protein. It is preferable to mix the blood component with the solution of osteogenic protein prior to addition of the porous particles.

Additional optional components useful in the practice of the subject application include, e.g. cryogenic protectors such as mannitol (to protect from degradation during lyophilization), preservatives, antioxidants, etc. Of course, the traditional preparation of formulations in pharmaceutically acceptable form (i.e. pyrogen free, appropriate pH and isotonicity, sterility, etc.) is well within the skill in the art and is applicable to the formulations of the subject invention. The osteogenic protein and porous particles of the formulations may be provided to the clinic as a single vial formulation, either as a solution or in lyophilized form, or the formulation may be provided as a multicomponent kit wherein, e.g. the osteogenic protein is provided in one vial and the porous particles are provided in a separate vial. The blood to be used in the formulation is admixed at a time prior to use sufficient to allow clotting, generally 30 to 180 minutes prior to use, taking into account the well-known patient-to-patient variability in clotting time.

The formulations of the subject invention provide malleable implants that allow therapeutically effective amounts of osteoinductive protein to be delivered to an injury site where cartilage and/or bone formation is desired. Such an implant may be used as a substitute for autologous bone graft in fresh and nonunion fractures, spinal fusions, and bone defect repair in the orthopaedic field; in cranio/maxillofacial reconstructions; for prosthesis integration, especially as a surface coating; and in the dental field for erosion of the alveolar ridge an periodontal disease. In certain of these uses, the compositions of the subject invention may be used in combination with various bone cements, including erodible bone cements such as poly(propylene-cofumarate). Also, certain of these uses will utilize bioerodible hardware such as erodible plates, screws, etc. As alluded to above, the dosage regimen will be determined by the clinical indication being addressed, as well as by various patient variables (e.g. weight, age, sex) and clinical presentation (e.g. extent of injury, site of injury, etc.).

What is claimed is:

1. A composition comprising a pharmaceutically acceptable admixture of;
   (i) an osteogenic protein in an amount effective to stimulate osteogenic activity of infiltrating progenitor cells;
   (ii) an amount of porous particulate polymer matrix effective to adsorb said osteogenic protein; and
   (iii) an osteogenic protein-sequestering amount of autologous blood clot wherein the ratio of blood to porous particles useful herein is 1:1 to 1:2 (V:V): whereby desorption of the protein from the matrix is prevented and infiltration of progenitor cells into the matrix is allowed.

2. The composition of claim 1 wherein the osteogenic protein is selected from the group consisting of the members of the BMP-family.

3. The composition of claim 2 wherein the osteogenic protein is BMP-2.

4. The composition of claim 1 wherein the admixture is free from antifibrinolytic agents.

5. The composition of claim 2 wherein the admixture is free from antifibrinolytic agents.

6. The composition of claim 3, wherein the admixture is free from antifibrinolytic agents.

7. The composition of claim 1 wherein the polymer matrix component is selected from the group consisting of poly(lactic acid), poly(glycolic acid), and copolymers of lactic acid and glycolic acid.

8. The composition of claim 1 wherein the polymer matrix component is PLGA.

9. The composition of claim 2 wherein the polymer matrix component is PLGA.

10. The composition of claim 3 wherein the polymer matrix component is PLGA.

11. The composition of claim 4 wherein the polymer matrix component is PLGA.

12. The composition of claim 5 wherein the polymer matrix component is PLGA.

13. The composition of claim 6 wherein the polymer matrix component is PLGA.

14. The composition of claim 1 wherein the polymer matrix component is selected from polyorthoester, polyanhydride and poly(propylene-co-fumarate) polymers.

15. The composition of claim 2 wherein the polymer matrix component is selected from polyorthoester, polyanhydride and poly(propylene-co-fumarate) polymers.

16. The composition of claim 3 wherein the polymer matrix component is selected from polyorthoester, polyanhydride and poly(propylene-co-fumarate) polymers.

17. The composition of claim 4 wherein the polymer matrix component is selected from polyorthoester, polyanhydride and poly(propylene-co-fumarate) polymers.

18. The composition of claim 5 wherein the polymer matrix component is selected from polyorthoester, polyanhydride and poly(propylene-co-fumarate) polymers.

19. The composition of claim 6 wherein the polymer matrix component is selected from polyorthoester, polyanhydride and poly(propylene-co-fumarate) polymers.

20. A composition comprising a pharmaceutically acceptable admixture of
   (i) BMP-2 in an amount effective to stimulate osteogenic activity of infiltrating progenitor cells;
   (ii) a polymeric matrix component comprising polymeric particles having a diameter of about 140 and 850 microns and a porosity such that the surface area of the particles is between about 0.01 to 4.0 $m^2/g$, wherein the polymer is selected from the group consisting of poly(lactic acid), poly(glycolic acid), and copolymers of lactic acid and glycolic acid; and
   (iii) a protein sequestering amount of autologous blood clot wherein desorption of the protein from the matrix is prevented and infiltration of progenitor cells into the matrix is allowed.

* * * * *